US006610862B2

(12) United States Patent
Bercovici et al.

(10) Patent No.: US 6,610,862 B2
(45) Date of Patent: Aug. 26, 2003

(54) PREPARATION OF WARFARIN SODIUM FROM WARFARIN SODIUM-2-PROPANOL CLATHRATE BY SOLVENT EXPULSION

(75) Inventors: Sorin Bercovici, Kiriat Ono (IL); Shimon Chernyak, Yokneam Ilit (IL); Konstantin Ulanenko, Natania (IL)

(73) Assignee: Taro Pharmaceutical Industries Ltd., Haifa Bay (IL)

(*) Notice: Subject to any disclaimer, the term of this patent is extended or adjusted under 35 U.S.C. 154(b) by 0 days.

(21) Appl. No.: 09/794,207

(22) Filed: Feb. 28, 2001

(65) Prior Publication Data

US 2002/0120156 A1 Aug. 29, 2002

(51) Int. Cl.$^7$ ............................................. C07D 311/02
(52) U.S. Cl. ..................................... 549/285; 514/457
(58) Field of Search ........................... 549/285; 514/457

(56) References Cited

U.S. PATENT DOCUMENTS

| | | | |
|---|---|---|---|
| 2,427,578 A | 9/1947 | Stahmann et al. | 549/285 |
| 2,752,360 A | 6/1956 | Starr et al. | 549/285 |
| 2,765,321 A | 10/1956 | Schroeder et al. | 549/285 |
| 2,777,859 A | 1/1957 | Link et al. | 549/285 |
| 3,077,481 A | 2/1963 | Schroeder et al. | 549/285 |
| 3,192,232 A | 6/1965 | Schroeder et al. | 549/285 |
| 3,239,529 A | 3/1966 | Preis et al. | 549/285 |
| 3,246,013 A | 4/1966 | Weiner et al. | 549/285 |
| 4,113,744 A | 9/1978 | Badran | 549/285 |
| 4,818,297 A | 4/1989 | Holzmüller et al. | 134/12 |
| 4,826,689 A | 5/1989 | Violanto | 424/489 |
| 5,686,631 A | 11/1997 | Li et al. | 549/285 |
| 5,696,274 A | 12/1997 | Uwaydah et al. | 549/285 |
| 5,856,525 A | 1/1999 | Li et al. | 549/286 |

FOREIGN PATENT DOCUMENTS

| | | | | |
|---|---|---|---|---|
| FR | 1397213 | 12/1963 | | 549/285 |
| WO | WO 97/03062 | 1/1997 | | 549/285 |
| WO | WO 97/24347 | 7/1997 | | 549/285 |

OTHER PUBLICATIONS

12$^{th}$ Edition, 10174. "Warfarin", pp. 1715 (1996).
Kleemann & Engel, et al. "Pharmaceutical Substances" 3$^{rd}$ Ed (English), p. 2010 (1999).
Ohnishi, "Structure–Activity Relationship between the Hydrophobicity of Alkali metal Salts of Warfarin [3–(α–Acetonyl–benzyl)–4–hydroxycoumarin] and the Effectiveness of the Taste Response to These Salts in Mice", Biosci. Biotech. Biochem., 59 (6), 995–1001. 1995.
Ivanov, "New Efficient Catalysts in the Synthesis of Warfarin and Acenocoumarol", Arch. Pharm (Weinheim), 1990, 323, pp. 521–522.
Bush et al, "High yield Synthesis of Warfarin and Its Phenolic Metablites: New Compounds", Journal of Pharmaceutical Sciences, vol. 72, No. 7, pp. 830–831, Jul. 1983.

Seidman et al, "Studies on 4–Hydroxycoumarins. X. Acylation of 3–(α–Phenyl–β–acetylethyl)–4–hydroxycoumarin", Journal of American Chemical Society, Nov. 1950, pp. 5193–5195.
Ikawa et al, "Studies on 4–Hydroxycoumarins. V. The Condensation of α, β–Unsaturated Ketones with 4–Hydroxycoumarin", Journal of American Chemical Society, 1944, pp. 902–906.
"Warfarin Sodium", Pharmaceutical Manufacturing Encyclopedia, 2$^{nd}$ Ed., vol. 2, 1988, pp. 1590–1591.
Hiskey et al, "Clathrates of Sodium Warfarin" Journal of Pharmaceutical Science, 1965, pp. 1298–1302.
Demir, Ayhan S., et al., "Enantioselective Synthesis of 4–Hydroxy–3–(3–Oxo–1–Phenyl Butyl)–2H–1–Benzopyran–2–One (Warfarin)," Turk. J. Chem., pp. 139–145 (1996).
Joshi, C.G., et al., "Studies in the Synthesis of Warfarin [3–(α–Acetonylbenzyl)–4–hyroxycoumarin], " Indian J. Technol., pp. 461–462 (1972).
Finn, Sidney Louis, "Thermogravimetric Analysis of Sodium Warfarin Isopropanol Clathrate (i:4:0)," A Thesis Submitted to the Graduate Faculty of the North Dakota State University of Agriculture and Applied Sciences, Jul. 1977, Diss. Abstr. Int. B, 1978, 38 (12 Pt. 1), 5951.
Robinson, Andrea, et al., "The First Practical Asymmetric Synthesis of R and S–Warfarin," Tetrahedron Letters., vol. 37, No. 46, pp. 8321–8324 (1996).
Gao, Danchen, et al., "Use of Solution Calorimetry to Determine the Extent of Crystallinity of Drugs and Excipients," International Journal of Pharmaceutics, 151, pp. 183–192 (1997).
Gao, Danchen, et al., "Physical Chemical Stability of Warfarin Sodium," AAPS Pharmaci, 2001, pp. 1–8 (Jan. 16, 2001).
Özcan, Eyüp, et al., "The Factors Effecting the Reaction Efficiency in Warfarin Synthesis," Journal Marmara Univ. Fen Bilimleri Derg., vol. 6, pp. 155–67 (1989) (article and citation attached).

(List continued on next page.)

Primary Examiner—Alan L. Rotman
Assistant Examiner—Raymond Covington
(74) Attorney, Agent, or Firm—Venable; Michael A. Gollin; Keith G. Haddaway

(57) ABSTRACT

The present invention is a method for producing warfarin sodium from warfarin sodium 2-propanol clathrate by thermal, nondestructive solvent expulsion. The solvent expulsion is conducted under conditions of controlled heat transfer whereby the 2-propanol is expelled from the warfarin sodium 2-propanol clathrate without decomposition of warfarin sodium or the clathrate. Heating is conducted the clathrate at a temperature from about 100° C. to about 170° C. in an active oven under air or in an inert atmosphere and at partial pressures ranging from that of a relative vacuum to atmospheric pressure. The invention also relates to pure warfarin sodium prepared according to the method of the invention and pharmaceutical compositions containing warfarin sodium.

40 Claims, No Drawings

OTHER PUBLICATIONS

Yang, Tsang–Hsiung, et al., "Synthesis of Anticoagulants, Dicumarol and Warfarin," *Tai–wan K'o Hseu*, pp. 1–7 (1984).

Manolov, I., et al., Synthesis and Antimetastic Properties of 4–hydroxy–3(3–oxo–1–phenylbutyl–2H–1–benzopyran–2–one (Warfarin), *Farmatsiya (Sofia)*, pp. 1–6 (1990) (English abstract).

Xu, Xinyuan, "The Identification of Principal Components of Clathrate and Complex with Infrared Spectral Subtraction Method," *Chinese Journal of Pharmaceutical Analysis (China)*, vol. 17, pp. 87–89 (Mar. 1997) (English abstract).

PREPARATION OF WARFARIN SODIUM FROM WARFARIN SODIUM-2-PROPANOL CLATHRATE BY SOLVENT EXPULSION

BACKGROUND OF THE INVENTION

1. Field of the Invention

The present invention relates to a process for preparation of warfarin sodium. More specifically, the present invention relates to a process for preparing warfarin sodium from warfarin sodium 2-propanol clathrate by solvent expulsion.

2. Background

Warfarin sodium, known by the chemical name 4-hydroxy-3-(3-oxo-1-phenylbutyl)-2H-1-benzopyran-2-one sodium salt, is a well established, widely used oral anticoagulant and rodenticide. (See, for example, U.S. Pat. No. 4,113,744 issued Sep. 12, 1978.)

According to U.S. Pat. No. 3,192,232, warfarin sodium prepared by existing methods often has as undesirable slight yellow color. (See also, U.S. Pat. No. 3,077,481).

U.S. Pat. No. 3,246,013 also emphasizes the difficulties encountered with the preparation of a high purity warfarin sodium. This patent discloses that the removal of the 2-propanol solvent from warfarin sodium 2-propanol clathrate cannot be achieved even with heating at 100° C. over $P_2O_5$ for 3–5 hours in a high vacuum (0.1 mm Hg). U.S. Pat. No. 3,077,481 further discloses that heating the clathrate at higher temperatures (145° C.) in air at a high vacuum (1.0 mm Hg) for prolonged time periods (24 hours) results in undesirable decomposition. Also, heating at still higher temperatures (230° C.), while successfully removing 2-propanol from the clathrate, results in rapid decomposition.

The present process is contrary to these teachings and provides a flexible and cost effective method of preparing warfarin sodium from warfarin sodium 2-propanol clathrate, using a single vessel, in one step, and yielding directly a pure, dry, pharmacopoeia grade substance.

The present process avoids complications and difficulties encountered in the prior art procedures, for example, the use of alkaline aqueous media and decomposition of warfarin sodium previously encountered in the prior art.

This invention succeeds where previous efforts have failed and presents a simple synthesis of warfarin sodium from warfarin sodium 2-propanol clathrate.

SUMMARY OF THE INVENTION

In summary, the present invention is a method by which warfarin sodium may be easily prepared in a commercially feasible manner. Its purity makes it very useful in the pharmaceutical industry.

The present invention provides a process which is simple, cost effective and viable for manufacturing warfarin sodium from its parent 2-propanol clathrate.

The present invention is a method for producing pure warfarin sodium from warfarin sodium 2-propanol clathrate by thermal, nondestructive solvent expulsion. The solvent expulsion according to the present invention is achieved by heating warfarin sodium 2-propanol clathrate at a temperature from about 100° C. to about 170° C., preferably at a temperature of from about 130° C. to about 160° C. and more preferably at a temperature of from about 145° C. to about 155° C. under controlled heat transfer conditions.

The solvent expulsion may be accomplished by heating the clathrate in air or, preferably in an inert atmosphere. Preferred gases for the inert atmosphere are nitrogen and argon. The solvent expulsion may be conducted at partial pressures ranging from that of a relative vacuum to 760 mm Hg. Atmospheric pressure or a reduced pressure of from about 50 mm Hg to about 100 mm Hg are preferred. The solvent expulsion may take from about 2 to about 30 hours; in preferred embodiments, the solvent expulsion takes from about 6 hours to about 20 hours.

Controlled heat transfer conditions may be provided by heating in a suitable oven including, for example, a turbo oven, a vacuum tray oven, a paddle rotary oven, a fluid bed oven, other dynamic ovens, ovens that can move the sample in the oven, and others. A special turbo oven that includes the possibility of using an inert gas (nitrogen, argon, helium) blanket in the oven by incorporating an inlet-outlet valve purge system is preferred.

In another aspect, the invention relates to pure warfarin sodium produced by the method of the invention. The pure warfarin sodium contains less then about 0.5%, preferably less than 0.4% and more preferably less than about 0.2%, 2-propanol. The pure warfarin sodium contains less than about 1% non-solvent impurities. The invention also relates to a pharmaceutical composition comprising pure warfarin sodium produced by the method of the invention.

Further objectives and advantages will become apparent from a consideration of the description and non-limiting examples.

DETAILED DESCRIPTION OF THE PREFERRED EMBODIMENTS

In describing preferred embodiments of the present invention, specific terminology is employed for the sake of clarity. However, the invention is not intended to be limited to the specific terminology so selected. All references cited herein are incorporated by reference as if each had been individually incorporated.

"Pure" refers to a substance that meets the requirements of at least one of the US Pharmacopoeia ("USP"), the British Pharmacopoeia ("BP") and the European Pharmacopoeia ("EP").

The terms "clathrate" and "parent clathrate" are used to designate warfarin sodium 2-propanol clathrate.

It is to be understood that the terms "2-propanol", "isopropanol" and "IPA", as used in the art, all refer to the same chemical entity.

The tendency of the warfarin sodium 2-propanol clathrate starting material to decompose when exposed to relatively high temperatures over prolonged periods of time, especially when is not very pure, is a known phenomenon. It has been previously described that, where conditions requiring long and uncontrolled exposure times coupled with reduced pressure are used, decomposition inevitably results. The present invention overcomes these difficulties by expelling 2-propanol from warfarin sodium 2-propanol clathrate by using heat under controlled specific conditions (i.e. shorter time and higher temperature or longer time and higher temperature under an inert atmosphere).

According to the present invention, it has been found that warfarin sodium may be produced from the corresponding warfarin sodium 2-propanol clathrate by heating at a temperature below about 170° C., preferably not more than about 160° C., under conditions of controlled heat transfer. "Conditions of controlled heat transfer" or "means for controlled heat transfer" refer to a heating apparatus and condition whereby the starting material is heated relatively evenly and efficiently. Conditions of controlled heat transfer result in solvent expulsion without decomposition of the warfarin sodium or the parent clathrate. In contrast to previously available methods, and contrary to the expectations of a person skilled in the art, heating at high vacuum is unnecessary and, in fact, undesirable. It was found that significant decomposition occurred during the time required to remove the solvent when a high vacuum condition was used. Without being bound to any theory, it is thought that the use of a high vacuum reduces the amount of atmosphere circulating around the sample and hinders the evenness of heating. Thus, it was found that solvent expulsion is best accomplished at atmospheric pressure or, if a reduced pressure is used, at a pressure high enough to permit efficient heating. Alternatively, other means that permit efficient heating may be used at either atmospheric or reduced pressures.

The invention thus requires that the clathrate be heated at a temperature at which the solvent is completely expelled before significant decomposition occurs. For example, by conducting the solvent expulsion according to the invention, the solvent content may be reduced to less than about 0.5% before significant decomposition occurs. In a more preferred embodiment, the 2-propanol content may be reduced to less than about 0.4% and in the most preferred embodiment to less than about 0.2%. Pharmacopeias generally require less than 1.0% of total non-solvent impurities, and this is also readily achieved by the present invention.

To calibrate a given oven to a condition of controlled heat transfer according to the invention, the solvent expulsion is first conducted on a test batch. Aliquots are removed at predetermined times, for example each hour, and the solvent remaining and the extent of decomposition in the aliquot measured. If decomposition is occurring before solvent expulsion, conditions may be changed by, for example, lowering the temperature, lowering or increasing the pressure, or introducing an inert gas. The optimal conditions are thus determined. Samples are then subjected to heating under the same conditions. Using this methodology, it was found that samples of 50–100 g could be effectively prepared in 4–6 hours while larger samples, e.g. 12 kg, required about 24 hours of heating.

In order to heat the clathrate under a condition of controlled heat transfer, an appropriate oven must be used. Many types of drying ovens are used in the chemical industry and may be used to practice the invention. It has been found that a few ovens are particularly useful for practicing of the invention. In particular, it has been found that typical "static" drying ovens, i.e. ovens that operate at atmospheric pressure, without circulation of the atmosphere surrounding the sample, without agitation of the sample and without an inert atmosphere, are less effective at controlling the conditions of heat transfer sufficient to remove the solvent from the clathrate without causing decomposition. In general, the most appropriate ovens for practicing the inventions are active ovens that are capable of operating at a reduced pressure, circulating or moving the atmosphere surrounding the warfarin sodium 2-propanol clathrate, agitating the warfarin sodium 2-propanol clathrate or surrounding the warfarin sodium 2-propanol clathrate with an inert atmosphere. Examples of active ovens include:

- Turbo ovens of the standard commercial type that have trays for the substance (as a "fixed bed") while hot air circulates by the aid of a turbo fan at atmospheric pressure.
- Special turbo ovens that include the possibility of using an inert gas (nitrogen, argon, helium) blanket in the oven by incorporating an inlet-outlet valve purge system. Such an oven is particularly useful and preferred for practicing the invention on larger industrial scales.
- Vacuum tray ovens having a closed system and working under low pressure. These may be used, but are generally less suitable for practicing the invention on an industrial scale.
- Paddle rotary ovens which operate at atmospheric pressure, with or without inert gas blanket, in which the substance is stirred by the aid of a paddle type mixer inside the oven during the operation.
- Fluid bed ovens in which a gas circulates through the sample during heating and thus provide movement of the atmosphere in the oven relative to the substance being dried.

These ovens may be typical commercial ovens or may be specially modified. The process of the invention results in the expulsion of 2-propanol (solvent expulsion).

The solvent expulsion may be conducted at atmospheric pressure or at a reduced pressure. When conducting the solvent expulsion at atmospheric pressure in air, a turbo oven is preferred. More preferably, solvent expulsion conducted at atmospheric pressure is accomplished in an inert gas atmosphere such as nitrogen, argon or the like. Solvent expulsion in an inert atmosphere may be carried out in any type of oven which provides for such an opportunity. A turbo oven which provides for an inert atmosphere via an inlet-outlet valve purge system is particularly preferred. Preferably, solvent expulsion is conducted at a reduced pressure of approximately 50 mm Hg to about 100 mm Hg, either in air or in an inert gas atmosphere. Nitrogen and argon are particularly preferred inert gases. Depending on the temperature and pressure, the solvent expulsion is conducted over a period of time ranging from about 2 hours to about 30 hours, and is preferably conducted over a period of time of from about 6 hours to about 20 hours. The most preferred temperature for the solvent expulsion is from about 145° C. to about 155° C.

The warfarin sodium prepared according to the present invention is obtained in yields which are generally greater than 95% of theory, and the product is a obtained in a pure form, i.e. containing less than about 1.0% non-solvent impurities. The 2-propanol content of the warfarin sodium product is typically not more than about 0.5%, is preferably less than about 0.4%, and is most preferably less than about 0.2%. The warfarin sodium is obtained as a white powder and gives analytical and physical data identical to those reported for a substance in the literature.

The present invention is best understood in terms of the following non-limiting examples. It will be appreciated by those of ordinary skill in the art that the conditions set forth in the non-limiting examples may be varied to obtain optimum results by routine experimentation. Such variations and routine experimentation are within the scope of the invention and the methods for performing those experiments are well known to persons of ordinary skill in the art.

EXAMPLES

Example 1

A standard turbo type tray oven was charged with pharmacopoeia quality warfarin sodium 2-propanol clathrate (100 g). Heating at 145–155° C. for 7 hours gave warfarin sodium as a white powder.

Yield: 90 g (97% of theory) of pharmacopoeia grade substance.

IPA content: not more than 0.2%.

Example 2

A vacuum tray type oven was charged with pharmacopoeia quality warfarin sodium 2-propanol clathrate (100 g). A relative reduced pressure of 50–100 mm Hg was achieved and a slight nitrogen stream applied.

The material was heated to 150–160° C. for 22 hours to give warfarin sodium as a white powder.

Yield: 91 g (99% of theory) of pharmacopoeia grade substance.

IPA content: less than 0.5%

Example 3

A paddle type rotatory oven was charged with pharmacopoeia quality warfarin sodium 2-propanol clathrate (1000 g) and a slight stream of dry nitrogen applied. The clathrate was heated to about 145–150° C. for 20 hours and gave the desired warfarin sodium as a white powder.

Yield: 895 g (97% of theory) of pharmacopoeia grade substance.

IPA content: about 0.4%

Example 4

A turbo type tray oven provided with an inert gas inlet/outlet controller was charged with pharmaceutical grade warfarin sodium 2-propanol (2500 g). The oven was flushed with nitrogen. The material was heated to 155° C. under a constant, slight nitrogen flow for 24 hours to give warfarin sodium as a white powder.

Yield: 2203 g (96% of theory) of pharmacopoeia grade substance.

IPA content: not more than 0.2%

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for preparing pure warfarin sodium by solvent expulsion comprising:

heating warfarin sodium 2-propanol clathrate at a temperature of from about 100° C. to about 170° C., expelling 2-propanol without decomposition of warfarin sodium or warfarin sodium 2-propanol clathrate, obtaining pure warfarin sodium.

2. The method of claim 1, wherein the heating is at a temperature of from about 130° C. to about 160° C.

3. The method of claim 1, wherein the heating is at a temperature of from about 145° C. to about 155° C.

4. The method of claim 1, wherein the heating is conducted in air or in an inert atmosphere.

5. The method of claim 4, wherein the inert atmosphere is selected from the group consisting of nitrogen and argon.

6. The method of claim 1, wherein the solvent expulsion is conducted under a partial pressure of from relative vacuum to atmospheric pressure.

7. The method of claim 6, wherein the solvent expulsion is conducted at a partial pressure of from about 50 mm Hg to about 100 mm Hg.

8. The method of claim 1, wherein the solvent expulsion is conducted over a time of from about 2 hours to about 30 hours.

9. The method of claim 8, wherein the solvent expulsion is conducted over a time of from about 6 hours to about 20 hours.

10. The method of claim 1, wherein said heating step is carried out in an oven selected from the group consisting of a turbo oven, a paddle rotary oven, a vacuum tray oven, and a fluid bed oven.

11. The method of claim 10, wherein the turbo oven is provided with an inert gas inlet/outlet controller for introduction of an inert gas atmosphere.

12. The method of claim 1, wherein the solvent expulsion is conducted by heating warfarin sodium 2-propanol clathrate in a turbo oven at a temperature of from about 145° C. to about 155° C. for a period of time of about 7 hours.

13. The method of claim 1, wherein the solvent expulsion is conducted by heating warfarin sodium 2-propanol clathrate at a temperature of from about 150° C. to about 160° C. in a vacuum tray oven at a pressure of from about 50 mm Hg to about 100 mm Hg for a period of time of about 22 hours.

14. The method of claim 1, wherein the solvent expulsion is conducted by heating warfarin sodium 2-propanol clathrate in a paddle rotary oven at a temperature of from about 145° C. to about 150° C. in an inert atmosphere for a period of time of about 20 hours.

15. The method of claim 2, wherein the solvent expulsion is conducted by heating warfarin sodium 2-propanol clathrate in a turbo oven provided with an inert gas inlet/outlet controller for introduction of an inert gas atmosphere at a temperature of 155° C. for a period of time of about 24 hours.

16. The method of claim 15, wherein said heating is conducted in an inert atmosphere.

17. The method of claim 1, wherein the warfarin sodium contains less than about 0.5% 2-propanol.

18. The method of claim 1, wherein the warfarin sodium contains less than about 0.2% 2-propanol.

19. The method of claim 1, wherein the warfarin sodium contains less than about 1% non-solvent impurities.

20. A pharmaceutical composition comprising pure warfarin sodium prepared according to claim 1.

21. A composition comprising pure warfarin sodium prepared by a method comprising the step of heating warfarin sodium 2-propanol clathrate at a temperature of from about 100° C. to about 170° C. under conditions of controlled heat transfer.

22. The composition of claim 21, wherein the conditions of controlled heat transfer comprise an oven selected from the group consisting of a turbo oven, a paddle rotary oven, a vacuum tray oven, a fluid bed oven and an oven comprising a moving tray.

23. The composition of claim 21, prepared by heating warfarin sodium 2-propanol clathrate in a turbo oven at a temperature of from about 145° C. to about 155° C. for a period of time of about 7 hours.

24. The composition of claim 21, prepared by heating warfarin sodium 2-propanol clathrate at a temperature of from about 150° C. to about 160° C. in a vacuum tray oven at a pressure of from about 50 mm Hg to about 100 mm Hg for a period of time of about 22 hours.

25. The composition of claim 21, prepared by heating warfarin sodium 2-propanol clathrate in a paddle rotary oven at a temperature of from about 145° C. to about 150° C. in an inert atmosphere for a period of time of about 20 hours.

26. The composition of claim 21, prepared by heating warfarin sodium 2-propanol clathrate in a turbo type tray oven provided with an inert gas inlet/outlet controller for introduction of an inert gas atmosphere at a temperature of 155° C. in an inert atmosphere for a period of time of about 24 hours.

27. A pharmaceutical composition comprising the pure warfarin sodium of claim 21.

28. The composition of claim 21, wherein the warfarin sodium contains less than about 0.4% 2-propanol.

29. The composition of claim 21, wherein the warfarin sodium contains less than about 0.2% 2-propanol.

30. The composition of claim 21, wherein the warfarin sodium contains less than about 1% non-solvent impurities.

31. A method for preparing pure warfarin sodium comprising:

step for expelling 2-propanol from said warfarin sodium 2-propanol clathrate using means for controlled heat transfer; and step for isolating pure warfarin sodium.

32. The method of claim 31, wherein the expelling step comprises means for providing an inert gas atmosphere.

33. The method of claim 31, wherein the expelling step comprises means for providing at least a partial vacuum.

34. The method of claim 31, wherein the expelling step comprises means for providing a temperature of from about 130° C. to about 160° C.

35. The method of claim 31, wherein the expelling step comprises means for providing a temperature of from about 145° C. to about 155° C.

36. The method of claim 31, wherein the expelling step comprises means for providing a partial pressure of from about 50 mm Hg to about 100 mm Hg.

37. The method of claim 31, wherein means for controlled heat transfer comprises a means for agitating the warfarin sodium 2-propanol clathrate.

38. The method of claim 31, wherein the means for controlled heat transfer comprises a means for moving a gaseous atmosphere in a drying oven relative to the warfarin sodium 2-propanol clathrate.

39. A method for preparing pure warfarin sodium by solvent expulsion comprising:

heating warfarin sodium 2-propanol clathrate at a temperature of from about 145° C. to about 160° C. in an oven selected from the group consisting of a turbo oven, a paddle rotary oven, a vacuum tray oven, and a fluid bed oven, expelling 2-propanol without decomposition of warfarin sodium or warfarin sodium 2-propanol clathrate, obtaining pure warfarin sodium, said pure warfarin sodium containing less than about 0.4% 2-propanol and less than about 1% non-solvent impurities.

40. Warfarin sodium prepared according to the method of claim 39.

* * * * *